Figure 1:
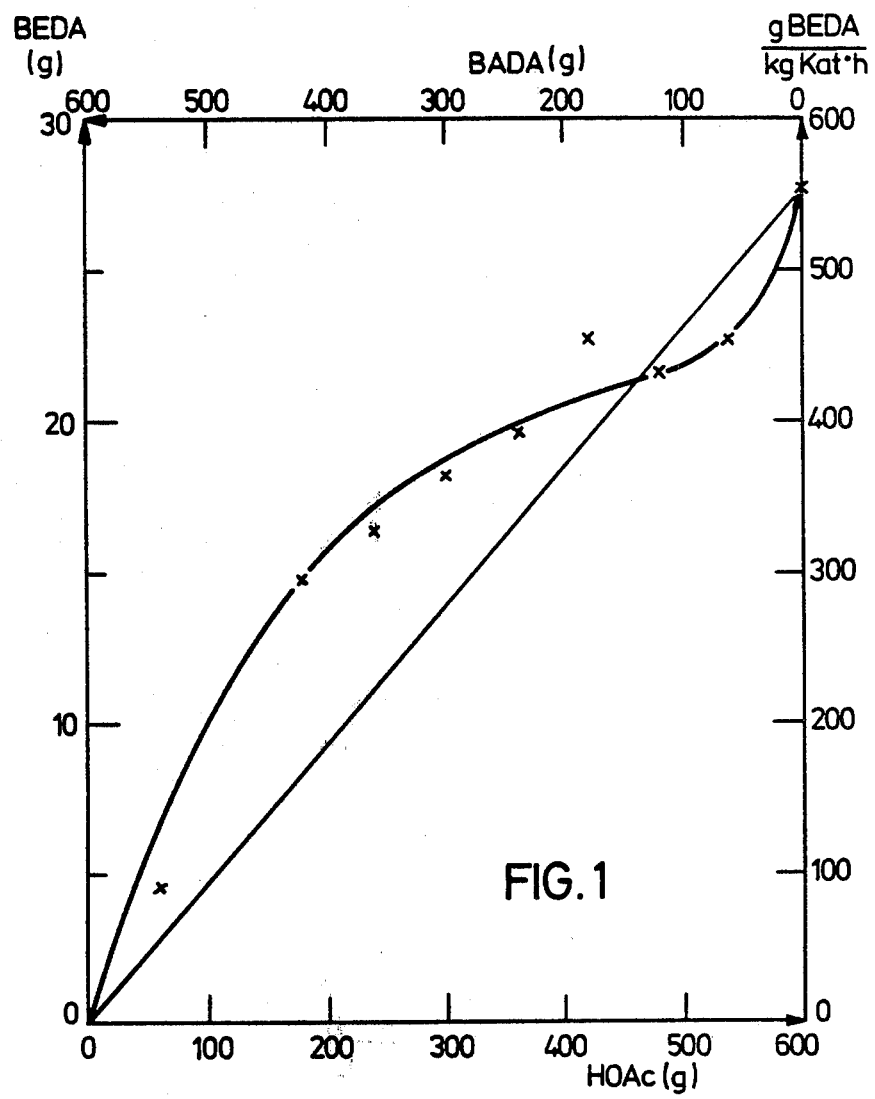

United States Patent [19]

Hartig et al.

[11] 4,262,139
[45] Apr. 14, 1981

[54] PREPARATION OF BUTENEDIOL DIACETATES AND OF BUTANEDIOL

[75] Inventors: Juergen Hartig, Gruenstadt; Hans-Martin Weitz, Bad Durkheim; Rolf Schnabel, Schifferstadt, all of Fed. Rep. of Germany

[73] Assignee: BASF Aktiengesellschaft, Fed. Rep. of Germany

[21] Appl. No.: 86,960

[22] Filed: Oct. 22, 1979

[30] Foreign Application Priority Data

Oct. 28, 1978 [DE] Fed. Rep. of Germany ....... 2847068

[51] Int. Cl.$^3$ .............................................. C07C 67/04
[52] U.S. Cl. .................................. 560/244; 568/858; 560/263
[58] Field of Search ................................ 560/244, 246

[56] References Cited

U.S. PATENT DOCUMENTS

| | | | |
|---|---|---|---|
| 3,755,423 | 8/1973 | Onoda | 560/244 |
| 3,922,300 | 11/1975 | Onoda | 560/244 |
| 4,010,197 | 8/1975 | Toriya | 560/263 |
| 4,026,924 | 5/1977 | Stapp | 560/246 |
| 4,122,285 | 10/1978 | Weitz | 560/244 |

FOREIGN PATENT DOCUMENTS 1138366 1/1969 United Kingdom ..................... 560/244
1494430 12/1977 United Kingdom .

*Primary Examiner*—Natalie Trousof
*Assistant Examiner*—Michael Shippen
*Attorney, Agent, or Firm*—Keil & Witherspoon

[57] ABSTRACT

A process for the preparation of butenediol diacetate by reacting butadiene with oxygen and acetic acid or with a compound which liberates acetic acid under the reaction conditions, over a solid catalyst which contains a platinum metal and one or more elements of main group 5 or 6, in the presence of butanediol diacetate, butanediol monoacetate, butanediol or a mixture of these, and the use of the butenediol diacetate, thus obtained, to prepare butane-1,4-diol by hydrogenating and then hydrolyzing the diacetate.

1 Claim, 3 Drawing Figures

PREPARATION OF BUTENEDIOL DIACETATES AND OF BUTANEDIOL

The present invention relates to a process for the preparation of butenediol diacetate by reacting butadiene with oxygen and acetic acid in the presence of a high-boiling solvent over a solid catalyst which contains a platinum metal and one or more elements of main group 5 or 6.

It is known, for example from German Laid-Open Application DOS No. 2,217,452, that carboxylic acid esters of an unsaturated diol may be prepared by reacting a conjugated diene with oxygen and a carboxylic acid over a solid catalyst which contains palladium and one or more of the elements antimony, bismuth, tellurium and selenium. According to German Laid-Open Application DOS No. 2,417,658, the reaction of butadiene with oxygen and acetic acid, to give butenediol diacetates, may also be carried out over a solid catalyst which contains platinum and one or more elements of main group 5 or 6.

The butenediol diacetates formed (BEDA) are cis- and trans-but-2-ene-1,4-diol diacetates (1,4-BEDA) and but-1-ene-3,4-diol diacetate (3,4-BEDA). Their boiling points, at atmospheric pressure, are respectively 227.2° C., 234.8° C. and 205.6° C. In general, the compounds derived from the 1,4-diol predominate.

In carrying out this reaction, referred to as acetoxylation, by conventional methods, certain peripheral conditions must be observed, which impose limits on the economics of the process in industrial operation. They especially include the solubility of oxygen in acetic acid and the need to remove an amount of heat of about 196 kJ/mole of BEDA (this heat being calculated on the assumption that the oxygen is gaseous and the other reactants are liquid). Further factors to be taken into account are polymer formation, the effect of the water formed during the reaction, the reaction temperature, the catalyst efficiency etc. Because of these limitations, the reaction mixture achievable in general contains only from 5 to 10% of BEDA, in addition to about 1% of water, the remainder being acetic acid. Because of the high boiling point of the butenediol diacetates, the latter can only be isolated from the reaction mixture by distilling off large amounts of acetic acid in addition to the water produced in stoichiometric amounts. Furthermore, it is necessary to dehydrate the water-diluted acetic acid, since, when the process is carried out continuously, the acetic acid is recycled to the synthesis stage and under these circumstances only small amounts of water can be tolerated. Finally, the water separated off must also be substantially freed from acetic acid. Since, as is known, distillation is one of the most energy-intensive process measures, the economics of the entire process become questionable.

It is an object of the present invention to provide a process wherein the energy requirement is substantially lower than in the conventional processes.

We have found that butenediol diacetate (BEDA), in particular 1,4-BEDA and 3,4-BEDA, can be prepared inexpensively by reacting butadiene with oxygen and acetic acid over a solid catalyst which contains a platinum metal and one or more elements of main groups 5 and 6, if the reaction is carried out in the presence of butanediol diacetate, butanediol monoacetate or butanediol, ie. the hydrogenation and hydrolysis products of butene-1,4-diol diacetate. These compounds all have boiling points (under atmospheric pressure) of about 229° C. The boiling points of the 1,2-diol and its compounds lie in a similar range.

In the conventional methods for the preparation of butenediol diacetates, the reaction is carried out in acetic acid, with the latter serving a double purpose, namely as a reactant and as a solvent (for butadiene and oxygen) or diluent. The acetic acid is therefore employed in very large excess, but as a result also causes the high energy consumption for working up, referred to above.

The compounds used according to the invention, ie. secondary products of the process in question, which in any case are ultimately formed in the course of the process, are able to take over the role of acetic acid as a solvent or diluent. They prove chemically inert under the acetoxylation reaction conditions or at most give acetic acid as a result of hydrolysis; furthermore, they are miscible with acetic acid.

The acetoxylation reaction can therefore now be carried out with the stoichiometric amount (based on butadiene employed) of acetic acid or of a compound which forms acetic acid, such as methyl acetate. Of course, it is possible to use an excess of acetic acid, and in general the process is operated with some excess thereof.

In fact, the following has been found: if the amount of acetic acid is reduced whilst retaining the other reaction conditions, there is indeed a reduction in the rate of reaction, but over a substantial range of mixing ratios, particularly interesting in practice, the reaction rate is substntially, ie. disproportionately, higher than corresponds to the proportion of acetic acid in the mixture. Accordingly, if in a series of experiments a part of the originally present acetic acid (HOAc) is systematically replaced by a corresponding amount of, for example, butanediol diacetate (BADA), the dependence shown in the attached FIG. 1 is found. This Figure does not require more detailed explanation—it may be seen immediately that the reaction rate (productivity P) is not proportional to the acetic acid concentration. This is all the more surprising since it is normally the objective of process development to manage without using additional solvent. The extent to which, in carrying out the acetoxylation industrially, the acetic acid is to be replaced by one of the solvents according to the invention, and the ratio of acetic acid/butadiene to be selected, can be determined by preliminary experiments. In principle any ratio can be used. In general, from 0.5 to 15, especially from 3 to 9, moles of acetic acid are employed per mole of butadiene. In the solvent mixture, the proportion of butanediol compounds, ie. of relatively high-boiling component, is in general from 4 to 80, especially from 20 to 70, % by weight, based on the chosen liquid reaction mixture. In the case illustrated in FIG. 1, the proportion is advantageously from 40 to 70%.

It can be advantageous to replace the acetic acid partially or completely by compounds which liberate acetic acid under the reaction conditions. Examples of suitable compounds of this type are the acetates of alcohols, in particular of monohydric alcohols, eg. methyl acetate, as well as butenediol monoacetate and/or diacetate, ie. the reaction product itself. These esters of acetic acid are used in place of acetic acid in the presence of a hydrolysis catalyst and of at least 1 mole of water per mole of butadiene to be reacted. The hydrolysis may take place before or during the acetoxylation of the butadiene.

Using the process according to the invention, the next stage after the acetoxylation is to remove unconverted compounds, or compounds formed, which can be separated off as gases (butadiene, butenes, CO₂ and possibly O₂). If desired, the unconverted acetic acid and water can also be removed at this stage. After conventional hydrogenation (for example as described in German Laid-Open Application DOS No. 2,537,890) of the butenediol derivatives formed, part is recycled and the remainder is, for example, hydrolyzed, acetic acid being removed where appropriate. Finally, butanediol or tetrahydrofuran are obtained as end products of such a process. In every case, the process according to the invention requires the working up of a substantially smaller amount of dilute acetic acid than in conventional processes.

The reaction on which the invention is based is carried out in the conventional manner over a solid catalyst which contains a platinum metal (ruthenium, rhodium, palladium, osmium, iridium or platinum, especially palladium and/or platinum), and one or more elements of main group 5 or 6, preferably antimony, bismuth, sulfur, selenium and tellurium, especially tellurium and antimony, but which may additionally contain iron metals, eg. nickel or iron. The catalyst is preferably supported, with carbon as the carrier. Depending on the catalyst arrangement, the process may be carried out with, for example, a fixed bed, suspended bed or fluidized bed, and either batchwise or, preferably, continuously. The reaction temperature is in general from 60° to 125° C., preferably from 80° to 100° C.; whilst temperatures below 60° C. are possible in principle, they give a lower conversion. Above 120° C., formation of by-products increases. The reaction pressure depends on the particular process arrangement chosen and is in general from atmospheric pressure to 100 bar.

The process according to the invention results in butenediol diacetates (BEDA). By-products detectable by gas chromatography are certain amounts (depending on the water content of the mixture) of hydrolysis products (ie. butenediol monoacetates and butenediols, which as a rule are also useful products), with only small amounts of products which cannot be isolated or utilized.

Instead of pure butadiene, butadiene-containing hydrocarbon mixtures may also be employed in the process. Particularly suitable hydrocarbon mixtures are C₄-hydrocarbon mixtures obtained as C₄-cracking cuts, since the butadiene contained in these is substantially cheaper than, for example, pure butadiene.

Such a C₄-cracking cut, which is obtained on cracking light naphtha, may in addition to 1,3-butadiene contain unsaturated and saturated hydrocarbons, eg. cis-but-2-ene, trans-but-2-ene, but-1-ene, iso-butene, iso-butane, n-butane and the like, but should, in order to avoid a reduction of the reaction rate and of the catalyst life, contain in total not more than 0.5% by volume of acetylenically unsaturated hydrocarbons.

The butenediol esters, especially butenediol diacetates, obtainable by the process of the invention are valuable intermediates, for example for the preparation of butanediol, tetrahydrofuran, adipodinitrile, hexamethylenediamine and vitamin A.

Figure 2:
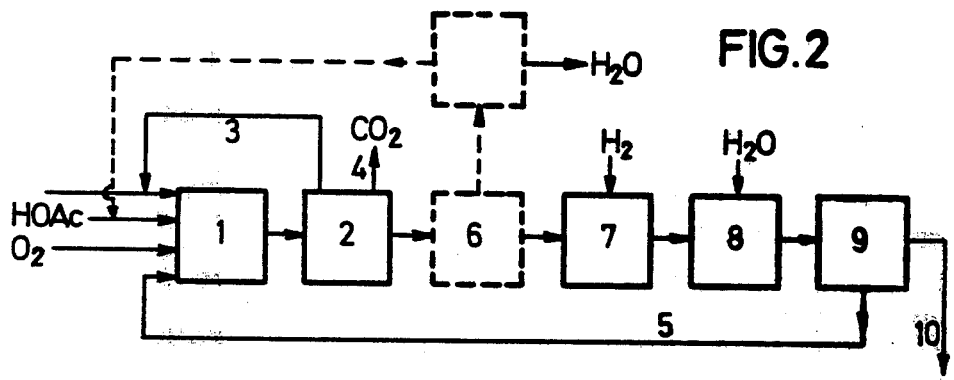

The flow chart (FIG. 2) shows the overall process according to the present invention.

In the first stage, butadiene, or a butadiene-containing C₄-cut (3) is reacted with acetic acid or a compound which gives acetic acid, and oxygen, over a suitable catalyst, in butanediol diacetate, butanediol monoacetate, butanediol or a mixture of these compounds as the solvent (5), to give butenediol diacetates.

Next, the excess butadiene is separated off (2) and recycled (3). If C₄-hydrocarbon mixtures have been used, butenes are removed at this stage. Oxides of carbon are also removed (4). If the oxygen has not been converted completely, it must also be removed before the hydrogenation. Where appropriate, the acetic acid still present in excess, as well as the water, may be removed from the desired product (6). This step is desirable if nickel or cobalt is used as the hydrogenation catalyst. On the other hand, removing acetic acid is not absolutely essential with noble metal catalysts. After hydrogenating (7) the butenediol derivatives formed to give butanediol derivatives, the reaction mixture obtained is hydrolyzed (8) and distilled (9). The greater part of the butanediol (10) then remains in the bottom of the downstream distillation column.

Figure 3:
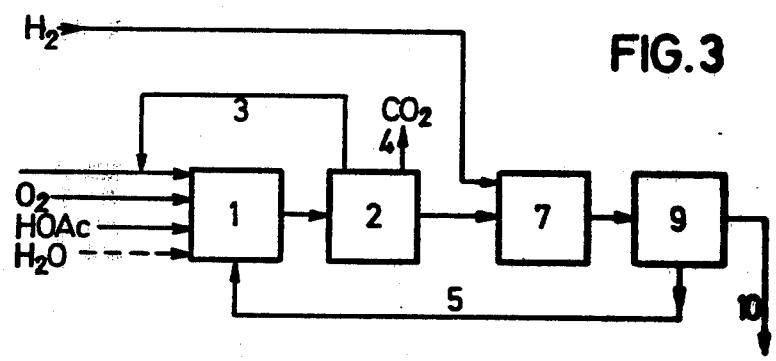

FIG. 3 shows a simplified method of carrying out the process; here the hydrolysis is carried out simultaneously with the synthesis. This method substantially avoids the occurrence of free acetic acid in the product streams.

EXAMPLE 1

Experiment 1 (Comparative Experiment)

To demonstrate the mode of operation of the invention, 12.5 g of a catalyst which contains 8.8% of palladium and 1.3% of tellurium on active charcoal (particle size 0.1–0.4 mm) and has been prepared as described in Example 33 of German Laid-Open Application DOS. No. 2,217,452 (cf. also Example 3) and 600 g of acetic acid, initially without diluent, are introduced into a reaction vessel fitted with a gassing stirrer (Experiment 1). A mixture of 3 liters (S.T.P.)/h of oxygen and 3 liters (S.T.P.)/h of butadiene is introduced at 95° C. After a reaction time of 4 hours under the stated conditions, the reaction is discontinued, the catalyst is separated off and the crude filtrate thereby obtained is examined by gas chromatography; furthermore, a liquid sample is taken hourly during the experiment. 27.7 g of butenediol diacetates (approximate composition 70% trans-1,4-BEDA, 20% cis-1,4-BEDA, 10% 3,4-BEDA) are found (this represents 554 g of BEDA/kg of catalyst.h).

TABLE 1

| Amount of diacetate in the reaction mixture (% by weight) in Experiment 1, as a function of time | | | |
|---|---|---|---|
| Time (h) | 3,4-BEDA | cis-1,4-BEDA | trans-1,4-BEDA |
| 1 | 0.17 | 0.27 | 0.84 |
| 2 | 0.32 | 0.54 | 1.80 |
| 3 | 0.55 | 0.89 | 2.92 |
| 4 | 0.53 | 0.90 | 2.99 |

Experiments 2 to 9

The procedure followed is as described in Experiment 1, the acetic acid being replaced stepwise by butane-1,4-diol diacetate, in the amounts shown in Table 2, whilst all other conditions are retained.

The Table also shows the results of this series of experiments. The last column gives the "catalyst productivity" of the particular experiment, in g of BEDA per kg of catalyst per hour. The distribution of the individual BEDA isomers corresponds to that shown in Table 1. FIG. 1 graphically shows the formation of BEDA in these experiments as a function of the amount of acetic acid and of butanediol diacetate (BADA).

TABLE 2

| Experiment No. | Acetic acid (g) | Butane-1,4-diol diacetate (g) | BEDA (g) | Space-time yield g of BEDA kg of cat.h |
|---|---|---|---|---|
| 1 | 600 | 0 | 27.7 | 554 |
| 2 | 540 | 60 | 22.7 | 454 |
| 3 | 480 | 120 | 21.7 | 433 |
| 4 | 420 | 180 | 22.7 | 453 |
| 5 | 360 | 240 | 19.6 | 392 |
| 6 | 300 | 300 | 19.2 | 385 |
| 7 | 240 | 360 | 16.4 | 327 |
| 8 | 180 | 420 | 14.8 | 295 |
| 9 | 60 | 540 | 4.5 | 91 |

EXAMPLE 2

Using conditions similar to Example 1, Experiment 6, 3.0 litersper hour of a mixture of equal parts by volume of butadiene and isobutene are introduced into a mixture of 300 g of butanediol diacetate and 300 g of acetic acid, all other conditions being retained. In the course of 4 hours, a total of 13.8 g of BEDA (space-time yield 277 g/kg of catalyst.h) are obtained. Table 3 shows the accumulation of butenediol diacetate in the reaction mixture.

TABLE 3

Time-dependence of the concentration of reaction products in the reaction mixture

| Time (h) | 3,4-BEDA (% by weight) | cis-1,4-BEDA (% by weight) | trans-1,4-BEDA (% by weight) |
|---|---|---|---|
| 0.5 | 0.05 | 0.02 | 0.34 |
| 1.0 | 0.07 | 0.08 | 0.54 |
| 1.5 | 0.11 | 0.12 | 0.76 |
| 2.0 | 0.14 | 0.15 | 0.91 |
| 2.5 | 0.18 | 0.21 | 1.16 |
| 3.0 | 0.22 | 0.24 | 1.37 |
| 3.5 | 0.24 | 0.28 | 1.49 |
| 4.0 | 0.28 | 0.34 | 1.70 |

EXAMPLE 3

(a) Preparation of the catalyst 42.57 g of $PdCl_2$ and 4.67 g of $TeO_2$, dissolved in 1 liter of hot 6 N hydrochloric acid, are added to 350 g of active charcoal (a commercial product sold under the name Desorex K, particle diameter 0.1–0.2 mm). The mixture is concentrated under reduced pressure on a rotary evaporator. The catalyst is then dried for 4 hours under nitrogen at 200° C., after which it is reduced for 24 hours at 200° C. and 24 hours at 400° C. in nitrogen containing methanol. According to elementary analysis, the finished catalyst contains 7.5% of palladium, 1.4% of tellurium and 0.7% of sulfur.

(b) Acetoxylation

The following components are introduced into a 1 liter shaken autoclave: 16.5 g of methyl acetate, 141.0 g of methanol, 4.0 g of $H_2O$, 207.8 g of butane-1,4-diol, 5.4 g of n-butanol, 0.5 g of acetic acid, 4.5 g of the above catalyst, 3.8 g of ion exchanger (Lewatit S 100 in the H+ form, from Bayer) and 20 ml of liquid butadiene.

Oxygen is forced in at room temperature to a pressure of 20 bar and the autoclave is shaken for 4 hours at 85° C. After the catalyst has been filtered off, the mixture is concentrated under reduced pressure. 211.5 g of a residue of the following composition are obtained:

0.08% of acetic acid
0.37% of but-1-ene-3,4-diol diacetate
0.15% of but-1-ene-3,4-diol
0.04% of butane-1,4-diol diacetate
0.03% of cis-but-2-ene-1,4-diol diacetate
2.74% of trans-but-2-ene-1,4-diol diacetate
91.32% of butane-1,4-diol
0.15% of trans-butene-1,4-diol monoacetate
1.36% of trans-butene-1,4-diol The amount of butenediol derivatives formed is 10.15 g. This corresponds to a space-time yield of 564 g of product/kg of catalyst.h.

We claim:

1. In a process for the preparation of butenediol diacetate in which butadiene is reacted with oxygen and acetic acid over a solid catalyst which contains a platinum metal selected from the group consisting of ruthenium, rhodium, palladium, osmium, iridium and platinum and one or more elements of the main group 5 or 6 selected from the group consisting of antimony, bismuth, sulfur, selenium and tellurium, the improvement which comprises:

carrying out the reaction in the presence of butanediol diacetate, butanediol monoacetate, butanediol or a mixture thereof.

* * * * *